United States Patent [19]

Biere et al.

[11] Patent Number: 4,855,295
[45] Date of Patent: Aug. 8, 1989

[54] TETRAHYDRO-BETA-CARBOLINES, AND THEIR USE AS DRUGS

[75] Inventors: Helmut Biere, Berlin, Fed. Rep. of Germany; Mogens Engelstoft, Vaerlose, Denmark; Andreas Huth, Berlin, Fed. Rep. of Germany; Dieter Rahtz, Berlin, Fed. Rep. of Germany; Ralph Schmiechen, Berlin, Fed. Rep. of Germany; Dieter Seidelmann, Berlin, Fed. Rep. of Germany; David N. Stephens, Berlin, Fed. Rep. of Germany

[73] Assignee: Schering Aktiengesellschaft, Berlin and Bergkamen, Fed. Rep. of Germany

[21] Appl. No.: 915,357

[22] Filed: Oct. 6, 1986

[30] Foreign Application Priority Data

Oct. 4, 1985 [DE] Fed. Rep. of Germany ....... 3535928

[51] Int. Cl.$^4$ .................. A61K 31/38; A61K 31/435; C07D 471/04
[52] U.S. Cl. .............. 514/232.8; 514/228.2; 514/255; 514/292; 544/60; 544/126; 544/361; 546/85; 546/86; 546/87
[58] Field of Search .............. 546/85, 86, 87; 544/60, 544/126, 361; 514/228.2, 232.8, 255, 292

[56] References Cited

U.S. PATENT DOCUMENTS 4,645,773 2/1987 Engelstoft et al. ................ 546/87

Primary Examiner—Mary C. Lee
Assistant Examiner—J. Richter
Attorney, Agent, or Firm—Millen, White & Zelano

[57] ABSTRACT

5,6,7,8-tetrahydro-beta-carbolines derivatives of formula I

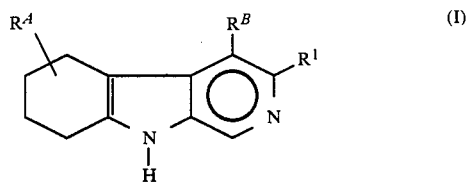

wherein
$R^1$ is an oxadiazolyl radical of the formula

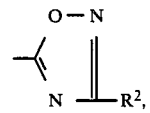

$COOR^3$ or $CONR^4R^5$,
$R^2$ is H, lower alkyl or cycloalkyl,
$R^3$ is H or lower alkyl,
$R^4$ and $R^5$ are H or lower alkyl, whereby $R^4$ and $R^5$ cannot be hydrogen at the same time, or $R^4$ and $R^5$ together with the adjacent nitrogen atom form a 5- or 6-member ring, which additionally can contain a heteroatom, and
$R^A$ is hydrogen, =O, cycloalkyl, —$COOR^3$ with $R^3$ having the above-mentioned meanings, or lower alkyl, which optionally can be substituted by OH, halogen, lower alkoxy, phenyl, phenyloxy, —$NR^4R^5$, whereby $R^4$ and $R^5$ have the above-mentioned meanings, and $R^B$ can be hydrogen, lower alkyl or lower alkoxyalkyl, have valuable pharmacological properties.

11 Claims, No Drawings

TETRAHYDRO-BETA-CARBOLINES, AND THEIR USE AS DRUGS

This invention relates to new 5,6,7,8-tetrahydro-beta-carbolines, their production and their use as medicaments.

SUMMARY OF THE INVENTION

It is an object of this invention to provide new compounds having valuable properties as medicaments.

Upon further study of the specification and appended claims, further objects and advantages of this invention will become apparent to those skilled in the art.

These objects have been achieved by providing compounds according to the invention of the formula I

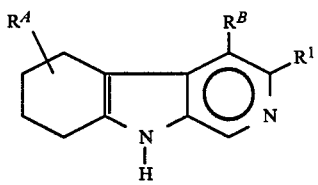

wherein H
$R^1$ is oxadiazolyl of the formula

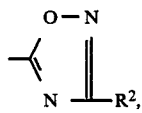

$COOR^3$, or $CONR^4R^5$
$R^2$ is H, lower alkyl or cycloalkyl,
$R^3$ is H or lower alkyl
$R^4$ and $R^5$ each independently is H, lower alkyl or hydroxylower-alkyl, but $R^4$ and $R^5$ cannot be hydrogen at the same time, or $R^4$ and $R^5$ together with the connecting nitrogen atom form a 5- or 6-member ring, which additionally can contain a heteroatom,
$R^A$ is hydrogen, =O, cycloalkyl, -$COOR^3$, lower alkyl, or lower alkyl substituted by OH, halogen (F, Cl, Br, I), lower alkoxy, phenyl, phenyloxy, or -$NR^4R^5$, wherein $R^3$, $R^4$ and $R^5$ have the above-mentioned meanings, and
$R^B$ is hydrogen, lower alkyl or lower alkoxyalkyl.

It is known that the strength of action of the betacarbolines depends on the intensity of their binding to the benzodiazepine receptor (C. Braestrup, M. Nielsen, J. Neurochem. 37, 333–341 (1981)). Further, it is known that for a high affinity for the benzodiazepine receptor, a planar aromatic system is necessary. Thus, for example norharman-3-carboxylic acid ethyl ester has proved to be considerably more effective than 1,2,3,4-tetrahydro-beta-carboline-3-carboxylic acid ethyl ester (H. A. Robertson et al. Eur. J. Pharmacol. 76, 281–284 (1981)).

Therefore, it was not to be expected that by eliminating the fully planar system of the beta-carbolines, compounds would be obtained which have a great affinity for the benzodiazepine receptor.

Surprisingly, it has now been found that the new 5,6,7,8-tetrahydro-beta-carbolines of formula I have an affinity for the benzodiazepine receptor comparable to the corresponding A ring aromatic beta-carboline derivatives.

The substituent $R^A$ of the new beta-carbolines can be in the 5, 6, 7 or 8 position. Substitution in the 5 or 6 position is preferred.

Typically, there can be from 0–4 non H substituents for $R^A$. Typically each of the four unsaturated carbon atoms in the A-ring will have only a single substituent. Preferably, there will be 1–2 substituents on the A-ring in total.

Suitable lower alkyl portions throughout include alkyl radicals of 1–4 carbon atoms, for example, methyl, ethyl, n-propyl, i-propyl, n-butyl, tert-butyl etc. Suitable cycloalkyl radicals throughout have 3–6 carbon atoms, for example, cyclopropyl, cyclobutyl, cyclopentyl, or cyclohexyl. For $R^2$, cyclopropyl is preferred as the cycloalkyl radical.

If $R^4$ and $R^5$ together form an alkylene bridge, which together with the nitrogen atom forms a heterocycle, then this 5–6-member ring can additionally contain an N, O or S atom, whereby oxygen is preferred. The following heterocycles can be mentioned as examples: piperidine, morphodine, pyrrolidine, thiomorpholine, piperazine, etc.

Typically, these heterocyclic rings are saturated, aliphatic moieties. They typically are bonded via a C-atom but can also be bonded by a N-hetero atom.

As lower alkyl radicals $R^A$ those with up to 2 carbon atoms are preferred. Preferred halogens are chlorine, bromine or iodine. The total number of C-atoms in alkoxyalkyl generally is 2–6.

The compounds according to the invention surprisingly show in pharmacological tests in comparison with 1,2,3,4-tetrahydro-beta-carbolines superior and, in comparison with aromatic compounds, at least equally good psychotropic properties.

The pharmacological properties of the compounds according to the invention were determined by investigation of their capacity to displace radioactively marked flunitrazepam from benzodiazepine receptors. The displacement activity of the compounds according to the invention is indicated as $IC_{50}$ and $ED_{50}$ values.

The $IC_{50}$ value indicates the concentration, which causes a 50% displacement of the specific binding of $^3$H-flunitrazepam (1.0 nM, 0° C.) in samples with a total volume of 0.55 ml of a suspension of brain membranes, e.g., of rats. The displacement test is performed as follows:

0.5 ml of a suspension of untreated rat brain in 25 mM $KH_2PO_2$, pH=7.1 (5–10 mg tissue/sample) is incubated for 40–60 minutes at 0° C. together with $^3$H-diazepam (specific activity 14.4 Ci/mmol, 1.9 nM) or $^3$H-flunitrazepam (specific activity 87 Ci/mmol, 1.0 nM). After incubation, the suspension is filtered through a glass filter, the residue is washed twice with cold buffer solution and the radioactivity is measured in the scintillation counter. The test is then repeated, but before addition of the radioactively marked benzodiazepine, a specific amount or an excess amount of the compound, whose displacement activity is to be determined, is added. Then the $IC_{50}$ value can be calculated on the basis of the values obtained.

The $ED_{50}$ value represents the dose of a test substance which causes a reduction of the specific binding of the flunitrazepam on the benzodiazepine receptor in a live brain to 50% of the control value. The in vivo test is performed as follows:

The test substance is injected into groups of mice in different doses and normally intraperitoneally. After 15 minutes the $^3$H-flunitrazepam is administered intravenously to the mice. After another 20 minutes the mice are sacrificed, their forebrain is removed and the radioactivity of the forebrains is measured by scintillation counting. The $ED_{50}$ value is determined from the dose-/action curve.

The new compounds of general formula I have valuable pharmacological properties. They act especially on the central nervous system and thus are suitable as psychotropic drugs in human medicine.

The compounds according to the invention can be used for formulation of pharmaceutical preparations, e.g., for oral and parenteral application in mammals including man, according to methods of galenics known in the art. As inactive ingredients for formulating of the pharmaceutical preparations those physiologically compatible organic and inorganic vehicles, which are inert in regard to the compounds according to the invention, are suitable for enteral and parenteral use.

Suitable vehicles include, for example, water, salt solutions, alcohols, polyethylene glycols, polyhydroxyethoxylated caster oil, gelatins, lactose, amylose, magnesium stearate, talc, silicic acid, fatty acid mono and diglycerides, pentaerythritol fatty acid ester, hydroxymethylcellulose and polyvinylpyrrolidone. The pharmaceutical preparations can be sterilized and/or mixed with inactive ingredients such as lubricants, preservatives, stabilizers, wetting agents, emulsifiers, buffering agents and dyes.

For parenteral application injection solutions or suspensions, especially aqueous solutions of the active compounds in polyhydroxyethoxylated castor oil, are especially suitable.

For oral application especially suitable are tablets, sugar-coated tablets or capsules with talc and/or a hydrocarbon vehicle or binding agent, such as, for example lactose, corn or potato starch. The administration can take place also in liquid form, as, for example, as a juice to which optionally a sweetening agent is added.

The compounds according to the invention are used in a unit dose of 0.05 to 100 mg of active substance in a physiologically compatible vehicle. The compounds according to the invention are administered in a dose of 0.1 to 300 mg/day, preferably 1-30 mg/day.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

All compounds of this invention have affinity for benzodiazepine receptors. Consequently, they have a spectrum of the activities of the benzodiazepines, e.g., muscle relaxant, sedative, anxiolytic or anticonvulsant and are useful for the conventional corresponding indications, e.g., muscle relaxants, antiepileptics, sedatives, hypnotics, tranquilizers, etc. These activities can be from agonistic to antagonistic to inverse agonistic, the corresponding indications being conventional in each case, e.g. antagonistically they can be used to reverse benzodiazepine effects, e.g., in cases of overdose, inverse agonistically they can be used to achieve the inverse effects of the benzodiazepines, e.g., they can be used as vigilance enhancers, etc. The type and level of activity for a given dosage of each compound can be conventionally determined by routine experimentation using well known pharmacological protocols for each of the activities; the corresponding indications treatable at that dosage will be well known to skilled workers based on the pharmacological results. The compounds of this invention are very useful as tranquilizers, anticonvulsants, antiaggressiveness agents, anxiolytics and for protection against stress. As such, they can be used for treatment of the following illustrative indications: anxiety and tension conditions, with and without depression; unrest; disturbances resulting from stress situations or an excess of stimulation, as well as pathological aggressiveness; etc.

The substances are also useful for the treatment of sleep disorders and for the treatment of spasticity and for muscle relaxation following anaesthesia. Compounds of thus invention are also useful for the treatment of memory disorders.

The production of the compounds according to the invention can take place according to processes known in the art, e.g., by hydrogenating a compound of formula II

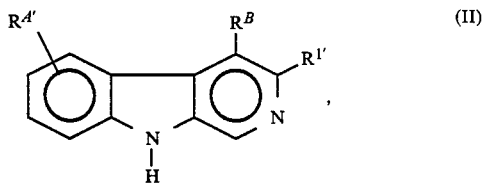

wherein
$R^B$ has the above-mentioned meanings,
$R^{1'}$ is —$COOR^3$ with $R^3$ having the above-mentioned meanings, and
$R^{A'}$ is hydrogen, a hydroxy group, cycloalkyl, —$COOR^3$, wherein $R^3$ has the above-mentioned meanings, or lower alkyl, which can be substituted with phenyl, lower alkoxy or hydroxy, in the presence of a catalyst, and optionally then etherifying compounds of formula I where $R^A$ is hydroxyalkyl with phenol, or in such compounds replacing the hydroxy group by secondary amines or by halogen, and then optionally aminating the halogen alkyl compound so obtained with an amine of the formula $HNR^4R^5$ with $R^4$ and $R^5$ having the above-mentioned meanings, or transesterifying, amidating or hydrolyzing an ester group wherein optionally the free acid thus obtained is amidized or converted to the tert-butyl ester or reacted with an amidoxime of the formula $R^2$-C(=NOH)NH$_2$, with $R^2$ having the above-mentioned meanings.

The hydrogenation can be performed in inert solvents, for example, alcohols, such as methanol, ethanol, propanol, butanol or in acids such as acetic acid or in ethers such as dioxane, diethyl ether in the presence of a catalyst. To avoid transesterifications, advantageously, the corresponding alcohol is used as solvent. All the usual hydrogenation catalysts are suitable catalysts, for example, Raney nickel or precious metal catalysts such as palladium or platinum, optionally on suitable supports such as carbon or calcium carbonate. Generally some acid such as acetic acid is added in the case of precious metal catalysts to accelerate the reaction. The hydrogenation can be performed at normal pressure or $H_2$ pressure up to 100 bar. The reaction temperature can be raised from room temperature to 100° C. (in working under pressure). After about 2-6 hours, the reaction is generally ended.

All the reactions optionally performed after the hydrogenation, take place according to processes known in the art.

For example, the hydroxyalkyl group $R^4$ can be halogenated by reaction with phosphorus tribromide or HBr to introduce bromine, reaction with thionyl chloride to introduce chlorine and reaction of the corresponding bromide or chloride with NaI to introduce iodine. The halogenation reaction can be performed with cooling to $-10°$ C. up to the boiling point of the solvent. Suitable solvents include all inert, preferably aphotic, solvents such, for example, chlorinated hydrocarbons such as dichloroethane, dichloromethane, chloroform or ethers such as diethyl ether, tetrahydrofuran, dioxane and ketones such as acetone, among others.

The halogenation can also be performed according to the method described by J. R. Falck and Sukumar Manna in Synthetic Communications, 15 (8), 663-8 (1985).

The halogenalkyl-beta-carbolines thus obtained can be converted, for example, with primary or secondary amines of the formula $HNR^4R^5$, with $R^4$ and $R^5$ having the above-mentioned meanings, into the corresponding aminoalkyl-beta-carboline derivatives.

Optionally, the stereoisomeric mixture resulting during the hydrogenation can be separated into its antipodes according to the usual methods, for example, chromatographically.

The production of phenoxyalkyl derivatives can take place, for example, using triphenylphosphine, azodicarboxylic acid diethyl ester and phenol. (M. S. Manhas et al. J. of the Chemical Society London 1975, pages 461-463). Analogously, the corresponding aminoalkyl derivatives can be produced according to this process by use of secondary amines.

The subsequent saponification of an ester group in the 3 position or in the A ring preferably takes place under alkaline conditions, in which the ester is heated with a diluted aqueous lye such as potassium or sodium hydroxide, in a protic solvent, for example, methanol, ethanol or ethylene glycol, to temperatures up to the reflux temperature of the reaction mixture.

The free beta-carboline carboxylic acids thus obtained are used, for example, for introduction of the 5-oxadiazolyl radical. For this purpose, the beta-carboline carboxylic acid is brought to condensation at the reflux temperature of the reaction mixture with an amidoxime of the formula $R^2-C(=NOH)NH_2$, in an inert solvent, which boils above 100° C. and is inert to the reactants. Suitable solvents for the condensation reaction are, for example, toluene and dimethylformamide. Advantageously, the free beta-carboline 3-carboxylic acid is suitably activated before the condensation reaction. For this purpose, the free acid can be converted into the mixed anhydride, into the activated ester or into the chloride. An activation with imidazole/thionyl chloride in an aprotic solvent such as dioxane, tetrahydrofuran, dimethylformamide or N-methylpyrrolidone at temperatures between 0° and 50° C., preferably room temperature, has proved efficient.

If a transesterification is desired, the reaction can be performed with the corresponding alcohol or alkali alcoholate, optionally titanium tetraisopropylate can be added as catalyst. The transesterification is usually performed at temperatures of 60° to 120° C. and it finished in about 2-6 hours.

The introduction of the tert-butyl ester group takes place, for example, by reaction of the carboxyl group with tert-butoxy-bis-dimethyl aminomethane. Generally the reaction is performed under inert gas atmosphere such as argon or nitrogen.

The corresponding amides can be produced from the abovedescribed beta-carboline carboxylic acids in a known way, for example, via the acid halides by reaction with primary or secondary amines.

The imidazolides obtained by reaction of the acids with the 1,1-carbonyldiimidazole are also suitable precursors for the preparation of the amides (Klaus P. Lippke et al. J. Pharmaceutical Sci. 74, 676-680 (1985)).

The starting materials are known or can be readily prepared from known starting materials according to processes known in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

5,6,7,8-Tetrahydro-5-ethoxymethyl-4-methyl-beta-carboline-3-carboxylic acid ethyl ester 5-Ethoxymethyl-4-methyl-beta-carboline-3-carboxylic acid ethyl ester (1 g) is shaken in ethanol (80 ml) with 10% palladium carbon (0.3 g) at a hydrogen pressure of 40 bars and a temperature of 70° C. for 2 hours. After filtering off of the catalyst, the reaction solution is evaporated, the residue is crystallized by treatment with a mixture of acetic acid and ethanol. The yield in 5,6,7,8-tetrahydro-5-ethoxymethyl-4-methyl-beta-carboline-3-carboxylic acid ethyl ester is 0.66 g.

Melting point, 222°-224° C.

Analogously there are produced:

5,6,7,8-tetrahydro-4,5-dimethyl-beta-carboline-3-carboxylic acid ethyl ester. Melting point, 103°-105° C..

5,6,7,8-tetrahydro-5-methoxymethyl-4-methyl-beta-carboline-3-carboxylic acid ethyl ester. Melting point, 200°-202° C..

5,6,7,8-tetrahydro-beta-carboline-3,5-dicarboxylic acid diethyl ester. Melting point, 214°-216° C.

5,6,7,8-tetrahydro-4-methyl-5-propoxymethyl-beta-carboline-3-carboxylic acid ethyl ester.

5,6,7,8-tetrahydro-4-methoxymethyl-beta-carboline-3-carboxylic acid ethyl ester. (Melting point, 174°-175° C. from $CH_2Cl_2$/acetone).

5,6,7,8-tetrahydro-4-methyl-5-oxo-beta-carboline-3-carboxylic acid ethyl ester. Melting point, 204°-206° C.

5,6,7,8-tetrahydro-5-ethoxymethyl-4-methoxymethyl-beta-carboline-3-carboxylic acid ethyl ester.

5,6,7,8-tetrahydro-5-ethoxymethyl-beta-carboline-3-carboxylic acid ethyl ester. Melting point, 190°-191° C. (from ethanol/ether).

Starting from completely aromatic isopropyl esters there were produced in isopropanol instead of ethanol, but otherwise according to example 1:

5,6,7,8-tetrahydro-5-ethyl-beta-carboline-3-carboxylic acid isopropyl ester. Melting point, 191°–93° C. (from diisopropyl ether).

5,6,7,8-tetrahydro-5-(1-hydroxyethyl)-beta-carboline-3-carboxylic acid isopropyl ester. Melting point, 177°–179° C. (from diisopropyl ether).

5,6,7,8-tetrahydro-5-ethoxymethyl-beta-carboline-3-carboxylic acid ethyl ester. Melting point, 273°–275° C..

5,6,7,8-tetrahydro-beta-carboline-3-carboxylic acid ethyl ester. Melting point, 224°–226° C..

5,6,7,8-tetrahydro-4-ethyl-beta-carboline-3-carboxylic acid ethyl ester. (Melting point, 198°–200° C. from hexane/acetone).

5,6,7,8-tetrahydro-4,5-dimethoxymethyl-beta-carboline-3-carboxylic acid ethyl ester

EXAMPLE 2

5,6,7,8-Tetrahydro-5-hydroxymethyl-4-methoxymethyl-beta-carboline-3-carboxylic acid ethyl ester 5-Hydroxymethyl-4-methoxymethyl-beta-carboline-3-carboxylic acid ethyl ester (0.5 g) is shaken in 80 ml of ethanol with Raney nickel under hydrogen with normal pressure and room temperature for 6 hours. Working up as in example 1. The yield in 5,6,7,8-tetrahydro-5-hydroxymethyl-4-methoxymethyl-beta-carboline-3-carboxylic acid ethyl ester is 0.3 g.

Analogously there is produced:
5,6,7,8-tetrahydro-5-hydroxymethyl-4-methyl-beta-carboline-3-carboxylic acid ethyl ester

EXAMPLE 3

510 mg of 4-methyl-beta-carboline-3-carboxylic acid ethyl ester is hydrogenated in 27 ml of ethanol and 3 ml of glacial acetic acid with 400 mg of palladium black at a hydrogen pressure of 10 bars at 75° C. for 5 hours. After filtering off of the catalyst, it is evaporated and is dispersed among methylene chloride and saturated sodium bicarbonate. The organic phase is washed with saturated hydrochloric acid solution, dried, filtered and concentrated. After chromatography over silica gel with methylene chloride/ethanol =5/1 and recrystallization from ethanol/hexane 130 mg of 5,6,7,8-tetrahydro-4-methyl-beta-carboline-3-carboxylic acid ethyl ester with a melting point of 244°–245° C. is obtained.

Analogously there are produced from 6-benzyl-4-methyl-beta-carboline-3-carboxylic acid ethyl ester:
5,6,7,8-tetrahydro-6-benzyl-4-methyl-beta-carboline-3-carboxylic acid ethyl ester (melting point of 196°–197° C. from ethanol/hexane)

from 6-cyclohexyl-4-methyl-beta-carboline-3-carboxylic acid ethyl ester:
5,6,7,8-tetrahydro-6-cyclohexyl-4-methyl-beta-carboline3-carboxylic acid ethyl ester (melting point, 198°–201° C.).

EXAMPLE 4

520 mg of 5,6,7,8-tetrahydro-4-methoxymethyl-beta-carboline-3-carboxylic acid is mixed in 20 ml of dimethylformamide with 32 ml of a freshly prepared 0.25 molar solution of thionyl diimidazole in tetrahydrofuran and stirred for 1 hour at room temperature. The resulting clear solution is mixed with 2.11 g of propionamidoxime and stirred for 2.5 hours at room temperature. After standing overnight it is concentrated, taken up in 30 ml of toluene and refluxed for 2 hours. After addition of 50 ml of water, it is shaken until a separated brown grease is dissolved and the toluene phase separated. The aqueous phase is extracted three times with 50 ml of ethyl acetate each and the collected organic phase is concentrated. The residue is first recrystallized from ethyl acetate/cyclohexane and then from ethanol/ethyl acetate.

147 mg of 3-(3-ethyl-1,2,4-oxadiazol-5-yl)-4-methoxymethyl-5,6,7,8-tetrahydro-beta-carboline with a melting point of 197°–199° C. is obtained.

EXAMPLE 5

0.7 g of 5-hydroxy-4-methoxymethyl-beta-carboline-3-carboxylic acid ethyl ester is hydrogenated in 50 ml of ethanol with 0.5 g of Raney nickel at a hydrogen pressure of 80 bars and a temperature of 100° C. for 6 hours. After filtering off of the catalyst, the solvent is evaporated in a vacuum. The residue is chromatographed on silica gel with dichloromethane and ethanol=10+1. 0.108 g of 4-methoxymethyl-5-oxo-5,6,7,8-tetrahydro-beta-carboline-3-carboxylic acid ethyl ester with a melting point of 249°–250° C. is obtained.

EXAMPLE 6

5.6.7.8-Tetrahydro-5-bromomethyl-4-methoxymethyl-beta-carboline-3-carboxylic acid ethyl ester From 5,6,7,8-tetrahydro-5-hydroxymethyl-4-methoxymethyl-beta-carboline-3-carboxylic acid ethyl ester (example 2) by reaction with phosphorus tribromide in dichloromethane.

EXAMPLE 7

5,6,7,8-tetrahydro-5-bromomethyl-4-methoxymethyl-beta-carboline-3-carboxylic acid ethyl ester (0.25 g) in dichloromethane (10 ml) is mixed with a solution of morpholine (1.0 ml) in ethanol (5 ml). The mixture is refluxed. After evaporation of the solvent, 5,6,7,8-tetrahydro-4-methoxymethyl-5-(4-morpholinyl)methyl-beta-carboline-3-carboxylic acid ethyl ester (0.1 g) can be isolated from the residue by chromatography on silica gel with a mixture of dichloromethane (19 parts) and ethanol (1 part). Melting point, 188°–191° C..

Analogously there are produced:
5,6,7,8-tetrahydro-5-diethylaminomethyl-4-methoxymethyl-beta-carboline-3-carboxylic acid ethyl ester
5,6,7,8-tetrahydro-5-diethanolaminomethyl-4-methoxymethyl-beta-carboline-3-carboxylic acid ethyl ester
5,6,7,8-tetrahydro-5-isopropylaminomethyl-4-methoxymethyl-beta-carboline-3-carboxylic acid ethyl ester.

EXAMPLE 8

0.5 g of 5,6,7,8-tetrahydro-5-ethoxymethyl-4-methyl-beta-carboline-3-carboxylic acid ethyl ester is refluxed in ethanol (40 ml) with 1 normal sodium hydroxide solution (3.5 ml) for 4 hours. After cooling, 1 normal acetic acid (3.5 ml) is added and evaporated. The evaporation residue is suspended in water, filtered off and washed well with water. 0.3 g of 5,6,7,8-tetrahydro-5-ethoxymethyl-4-methyl-betacarboline-3-carboxylic acid.

Analogously there are produced:
5,6,7,8-tetrahydro-4-methoxymethyl-5-(4-morpholinyl)methyl-beta-carboline-3-carboxylic acid
5,6,7,8-tetrahydro-4-methyl-5-(4-morpholinyl)methyl-beta-carboline-3-carboxylic acid.

EXAMPLE 9

5,6,7,8-tetrahydro-5-ethoxymethyl-4-methyl-beta-carboline-3-carboxylic acid tert-butyl ester 0.35 g of 5,6,7,8-tetrahydro-5-ethoxymethyl-4-methylbeta-carboline-3-carboxylic acid is heated in tert-butoxybis(dimethylamino)methane (8 ml) in an argon atmosphere for 3 hours to 120° C. After evaporation of the volatile ingredients the residue is chromatographed on silica gel with a mixture of dichloromethane (8 parts), acetone (1 part) and ethanol (1 part). The yield is 0.2 g.

EXAMPLE 10

0.2 g of 4-methoxymethyl-5-oxo-5,6,7,8-tetrahydro-betacarboline-3-carboxylic acid ethyl ester is refluxed in 10 ml of isopropanol with 0.1 ml of titanium tetraisopropylate for 1.5 hours under argon atmosphere. The crystals precipitated after cooling are sectioned off and rewashed with isopropanol. 0.135 g of 4-methoxymethyl-5-oxo-5,6,7,8 -tetrahydro-beta-carboline-3-carboxylic acid isopropyl ester with a melting point of 243°–245° C. is obtained.

EXAMPLE 11

1.15 g of 5,6,7,8-tetrahydro-4-methoxymethyl-betacarboline-3-carboxylic acid ethyl ester is refluxed in 45 ml of ethanol with 5 ml of 2N aqueous potassium hydroxide solution for 2 hours. After cooling, it is acidified with glacial acetic acid. The precipitated product is suctioned off; the mother liquor is concentrated to approximately 30 ml. The precipitated product is again suctioned off. 1 g of 5,6,7,8-tetrahydro-4-methoxymethyl-beta-carboline-3carboxylic acid with a melting point greater than 260° C. is obtained.

Analogously there are produced:

5,6,7,8-tetrahydro-4,5-dimethyl-beta-carboline-3-carboxylic acid 5,6,7,8-tetrahydro-5-methoxymethyl-4-methyl-betacarboline-3-carboxylic acid.

EXAMPLE 12

5,6,7,8-tetrahydro-5-ethoxymethyl-3-(3-ethyl-1,2,4-oxadiazol5-yl)-4-methyl-beta-carboline Thionyl dimidazolide (approximately 2.5 ml) in tetrahydrofuran (10 ml) is added to a suspension of 5,6,7,8-tetrahydro-5-ethoxymethyl-4-methyl-beta-carboline-3-carboxylic acid (0.36 g) in tetrahydrofuran (10 ml). After one hour propionamidoxime (0.4 g) is added to the solution. After 2 hours at room temperature the mixture is concentrated in a vacuum, water (25 ml) is added and the solution is extracted with dichloromethane. The organic phase is evaporated in a vacuum, the residue is heated with p-xylene (25 ml) under nitrogen for 2 hours at 160° C. After concentration in a vacuum the remaining residue is chromatographed on silica gel with methylene chloride.

5,6,7,8-Tetrahydro-5-ethoxymethyl-3-(3-ethyl-1,2,4-oxadiazol-5-yl)-4-methyl-beta-carboline (0.10 g) is obtained in the form of colorless crystals by treatment with petroleum ether.

Analogously there are produced:

5,6,7,8-tetrahydro-4,5-dimethyl-3-(3-ethyl-1,2,4-oxadiazol-5-yl)-beta-carboline 5,6,7,8-tetrahydro-3-(3-ethyl-1,2,4-oxadiazol-5-yl)-5-methoxymethyl-4-methyl-beta-carboline Analogously there are produced:

5,6,7,8-tetrahydro-5-ethoxymethyl-3-(3-ethyl-1,2,4-oxadiazol-5-yl)-4-methoxymethyl-beta-carboline. Melting point, 171°–173° C.

5,6,7,8-tetrahydro-3-(3-ethyl-1,2,4-oxadiazol-5-yl)-4-methoxymethyl-5-(4-morpholinyl)methyl-beta-carboline

EXAMPLE 13

5,6,7,8-tetrahydro-3-(3-ethyl-1,2,4-oxadiazol-5-yl)-4,5-dimethoxymethyl-beta-carboline Carbonyldiimidazole (0.85 g) is added to a suspension of 5,6,7,8-tetrahydro-4,5-dimethoxymethyl-beta-carboline-3-carboxylic acid (0.55 g) in absolute dimethylformamide (40 ml) at room temperature. The mixture is first stirred for 24 hours at room temperature and then for 5 hours at 60° C. Then propionamidoxine (0.64 g) is added at room temperature. The mixture is evaporated after 4 hours. The evaporation residue is refluxed in xylene on a water separator for 3 hours. After standing overnight, it is decanted from the undissolved, the undissolved is extracted twice with xylene. The combined extracts and original solution are evaporated, the residue is chromatographed on silica gel with a mixture of 95 parts of dichloromethane and 5 parts of methanol and, after recrystallization from ethanol yields the desired 5,6,7,8-tetrahydro-3-(3-ethyl-1,2,4-oxadiazol-5-yl)-4,5-dimethoxymethyl-beta-carboline (0.25 g). Melting point, 175°–177° C.

Analogously there is produced:

5,6,7,8-tetrahydro-3-(3-ethyl-1,2,4-oxadiazol-5-yl)-4-methyl-5-(4-morpholinyl)-methyl-beta-carboline. Melting point, 223°–225° C.

EXAMPLE 14

5,6,7,8-tetrahydro-4-methoxymethyl-5-(4-morpholinyl)-methyl-beta-carboline-3-carboxylic acid ethyl ester 5,6,7,8-Tetrahydro-5-hydroxymethyl-4-methoxymethyl-beta-carboline-3-carboxylic acid ethyl ester (0.78 g) is dissolved in water-free tetrahydrofuran (15 ml). (Solution A).

Under argon protection azodicarboxylic acid diethyl ester (2.1 g) slowly is added to a solution of triphenylphosphine (3.2 g) in water-free tetrahydrofuran (65 ml) at 0° C. After 20 minutes stirring, lithium bromide (2.11 g) is added (solution B).

Solution A is added to solution B drop by drop at 0° C. The mixture is first stirred for one hour at 0° C., then 1.5 hours at room temperature. Morpholine (23.1 g) is added drop by drop to the mixture cooled again to 0° C. After 15 hours at room temperature it is evaporated, the evaporation residue is chromatographed on silica gel with a mixture of 95 parts of dichloromethane and 5 parts of ethanol.

The 5,6,7,8-tetrahydro-4-methoxymethyl-5-(4-morpholinyl)-methyl-beta-carboline-3-carboxylic acid ethyl ester crystallized with rubbing with ether. Melting point, 188°–191° C.

The yield is 0.81 g.

Analogously there is produced:

5,6,7,8-tetrahydro-4-methyl-5-(4-morpholinyl)-methyl-beta-carboline-3-carboxylic acid ethyl ester

EXAMPLE 15

5,6,7,8-Tetrahydro-5-ethoxymethyl-4-methoxymethyl-beta-carboline-3-carboxylic acid 5,6,7,8-Tetrahydro-5-ethoxymethyl-4-methoxymethyl-betacarboline-3-carboxylic acid ethyl ester (0.51 g) is refluxed in ethanol (25 ml) with 1 normal sodium hydroxide solution (4.3 ml) for 3 hours. Then the solution is mixed with 5.3 ml of 1N hydrochloric acid and evaporated. The residue is boiled out with ethanol, 0.49 g of 5,6,7,8-tetrahydro-5-ethoxymethyl-4-methoxymethyl-beta-carboline-3-carboxylic acid is obtained from the ethanol extract after treatment with carbon by evaporation. Melting point, 250° C. (decomposition).

Analogously there is produced:

5,6,7,8-tetrahydro-4,5-dimethoxymethyl-beta-carboline-3-carboxylic acid.

In addition to the compounds named in the examples the following compounds are particularly preferred:

5,6,7,8-tetrahydro-5-phenoxymethyl-beta-carboline-3-carboxylic acid ethyl ester 5,6,7,8-tetrahydro-5-methoxymethyl-4-methyl-betacarboline-3-carboxylic acid isopropylamide.

The preceding examples can be repeated with similar success by substituting the generically of specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 5, 6, 7, 8-Tetrahydro-beta-carboline of the formula

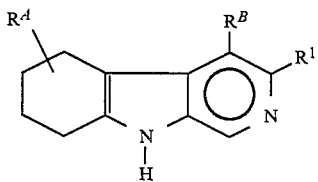

wherein $R^1$ is an oxadiazolyl of the formula

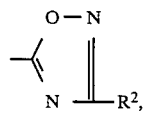

$COOR^3$ or $CON_4R^5$, $R^2$ is H, lower alkyl or $C_{3-6}$-cycloalkyl, $R^3$ is H or lower alkyl, $R^4$ and $R^5$ independently are H or lower alkyl, but $R^4$ and $R^5$ cannot be hydrogen at the same time, or $R^4$ and $R^5$ together with the connecting nitrogen atom form a piperidine, morpholine, pyrrolidine, thiomorpholine or piperazine group, $R^A$ is hydrogen, =O, $C_{3-6}$-cycloalkyl, -$COOR^3$, lower alkyl, or lower alkyl substituted by OH, halogen, lower alkoxy, phenyl, phenyloxy, or -$NR^4R^5$, and $R^B$ is hydrogen, lower alkyl or lower alkoxyalkyl.

2. A compound of claim 1 wherein $R^1$ is oxadiazolyl.

3. A compound of claim 1 wherein $R^1$ is $COOR^3$.

4. A compound of claim 1 wherein $R^1$ is $CONR^4R^5$.

5. A compound of claim 1 wherein $R^1$ is alkoxyalkyl or phenoxyalkyl.

6. 5,6,7,8-Tetrahydro-5-ethoxymethyl-4-methyl-beta-carboline-3-carboxylic acid ethyl ester, 5,6,7,8-tetrahydro-5-methoxymethyl-4-methyl-beta-carboline-3-carboxylic acid ethyl ester, 5,6,7,8-tetrahydro-beta-carboline-3,5-dicarboxylic acid diethyl ester, 5,6,7,8-tetrahydro-4-methyl-5-propoxymethyl-beta-carboline-3-carboxylic acid ethyl ester, 5,6,7,8-tetrahydro-4-methoxymethyl-beta-carboline-3-carboxylic acid ethyl ester, 5,6,7,8-tetrahydro-beta-carboline-3-carboxylic acid ethyl ester, 5,6,7,8-tetrahydro-4-ethyl-beta-carboline-3-carboxylic acid ethyl ester, 5,6,7,8-tetrahydro-4,5-dimethoxymethyl-beta-carboline-3-carboxylic acid ethyl ester, 5,6,7,8-tetrahydro-5-hydroxymethyl-4-methoxymethyl-beta-carboline-3-carboxylic acid ethyl ester, 5,6,7,8-tetrahydro-4-methyl-beta-carboline-3-carboxylic acid ethyl ester, 5,6,7,8-tetrahydro-6-benzyl-4-methyl-beta-carboline-3-carboxylic acid ethyl ester, 5,6,7,8-tetrahydro-6-cyclohexyl-4-methyl-beta-carboline-3-carboxylic acid ethyl ester, 5,6,7,8-tetrahydro-3-(3-ethyl-1,2,4-oxadiazol-5-yl)-4-methoxymethyl-beta-carboline, 5,6,7,8-tetrahydro-5-bromomethyl-4-methoxymethyl-beta-carboline-3-carboxylic acid ethyl ester, 5,6,7,8-tetrahydro--4-methoxymethyl-5-(4-morpholinyl)methyl-beta-carboline-3-carboxylic acid ethyl 5,6,7,8-tetrahydro-5-diethylaminomethyl-4-methoxymethyl-beta-carboline-3-carboxylic acid ethyl ester, 5,6,7,8-tetrahydro-5-diethanolaminoethyl-4-methoxymethyl-beta-carboline-3-carboxylic acid ethyl ester, 5,6,7,8-tetrahydro-5-isopropylaminomethyl-4-methoxymethyl-beta-carboline-3-carboxylic acid ethyl ester, 5,6,7,8-tetrahydro-5-ethoxymethyl-4-methyl-beta-carboline-3-carboxylic acid tert-butyl ester, 5,6,7,8-tetrahydro-4-methoxymethyl-5-oxo-beta-carboline-3-carboxylic acid isopropyl ester, 5,6,7,8-tetrahydro-5-ethoxymethyl--3-(3-ethyl-1,2,4-oxadiazol-5-yl)-4-methyl-beta-carboline, 5,6,7,8-tetrahydro-4,5-dimethyl-3-(3-ethyl-1,2,4-oxadiazol-5-yl)-beta-carboline, 5,6,7,8-tetrahydro-4-methoxymethyl-5-oxo-beta-carboline-carboxylic acid ethyl ester, 5,6,7,8-tetrahydro-4-methyl-5-oxo-beta-carboline-3carboxylic acid ethyl ester, 5,6,7,8-tetrahydro-5-ethoxymethyl-beta-carboline-3-carboxylic acid ethyl ester, 5,6,7,8-tetrahydro-5-ethyl-beta-carboline-3-carboxylic acid isopropyl ester, 5,6,7,8-tetrahydro-5-(1-hydroxyethyl)-beta-carboline-3-carboxylic acid isopropyl ester, 5,6,7,8-tetrahydro-5-ethoxymethyl-3-(3-ethyl-1,2,4-oxadiazol-5-yl)-4-methoxymethyl-beta-carboline, 5,6,7,8-tetrahydro-3-(3-ethyl-1,2,4-oxadiazol-5-yl)-4,5-dimethoxymethyl-beta-carboline, 5,6,7,8-tetrahydro-3-(3-ethyl-1,2,4-oxadiazol-5-yl)-4-methyl-5-(4-morpholinyl)-methyl-beta-carboline, 5,6,7,8-tetrahydro-5-ethoxymethyl-4-methoxymethyl-beta-carboline-3-carboxylic acid, 5,6,7,8-tetrahydro-4,5-dimethyl-beta-carboline-3-carboxylic acid ethyl ester,
5,6,7,8-tetrahydro-5-ethoxymethyl-4-methoxymethyl-beta-carboline-3-carboxylic acid ethyl ester,
5,6,7,8-tetrahydro-5-hydroxymethyl-4-methyl-beta-carboline-3-carboxylic acid ethyl ester
5,6,7,8-tetrahydro-5-ethoxymethyl-4-methyl-beta-carboline-3-carboxylic acid,
5,6,7,8-tetrahydro-4-methoxymethyl-5-(4-morpholinyl)methyl-beta-carboline-3-carboxylic acid,
5,6,7,8-tetrahydro-4-methyl-5-(4-morpholinyl)methyl-beta-carboline-3-carboxylic acid,
5,6,7,8-tetrahydro-4-methoxymethyl-beta-carboline-3-carboxylic acid,
5,6,7,8-tetrahydro-4,5-dimethyl-beta-carboline-3-carboxylic acid,
5,6,7,8-tetrahydro-5-methoxymethyl-4-methyl-beta-carboline-3-carboxylic acid,
5,6,7,8-tetrahydro-3-(3-ethyl-1,2,4-oxadiazol-5-yl)-4-methoxymethyl-5-(4-morpholinyl)methyl-beta-carboline,
5,6,7,8-tetrahydro-4-methyl-5-(4-morpholinyl)methyl-beta-carboline-3-carboxylic acid ethyl ester,
5,6,7,8-tetrahydro-4,5-dimethoxymethyl-beta-carboline-3-carboxylic acid,
5,6,7,8-tetrahydro-5-ethoxymethyl-4-ethyl-beta-carboline-3-carboxylic acid ethyl ester,
5,6,7,8-tetrahydro-3-(3-ethyl-1,2,4-oxadiazol-5-yl)-5-methoxymethyl-4-methyl-beta-carboline,
5,6,7,8-tetrahydro-5-phenoxymethyl-beta-carboline-3-carboxylic acid ethyl ester, or
5,6,7,8-tetrahydro-5-methoxymethyl-4-methyl-beta-carboline-3-carboxylic acid isopropylamide, each a compound of claim 1

7. A pharmaceutical composition comprising a compound of claim 1 and a pharmaceutically acceptable carrier.

8. A pharmaceutical composition comprising 0.05 to 100 mg of a compound of claim 1 and a pharmaceutically acceptable carrier.

9. A method of affecting the binding condition of benzodiazepine receptors comprising administering a compound of claim 1.

10. A method of achieving a tranquilizing effect comprising administering a compound of claim 1.

11. A method of achieving an anxiolytic effect comprising administering a compound of claim 1.

* * * * *

UNITED STATES PATENT AND TRADEMARK OFFICE
CERTIFICATE OF CORRECTION

PATENT NO. : 4,855,295

DATED : August 8, 1989

INVENTOR(S) : BIERE ET AL

It is certified that error appears in the above-identified patent and that said Letters Patent is hereby corrected as shown below:

Column 11, claim 1, line 55: reads "$COOR^3$ or $CON_4R^5$,"

should read -- $COOR^3$ or $CONR^4R^5$, --

Column 12, claim 6, line 35:

reads "carboline-3-carboxylic acid ethyl"

should read -- carboline-3-carboxylic acid ethyl ester, --

Column 12, claim 6, line 52:

reads "line-carboxylic acid ethyl ester, should read --line-3-carboxylic acid ethyl ester --

Signed and Sealed this

Seventeenth Day of July, 1990

*Attest:*

HARRY F. MANBECK, JR.

*Attesting Officer*     *Commissioner of Patents and Trademarks*